US005945276A

United States Patent [19]

Wu et al.

[11] Patent Number: 5,945,276

[45] Date of Patent: *Aug. 31, 1999

[54] REPORTER CELL LINE SYSTEM FOR DETECTING CYTOMEGALOVIRUS AND IDENTIFYING MODULATORS OF VIRAL GENE EXPRESSION

[75] Inventors: Jun Wu; Miguel S. Barbosa; Carla M. Suto, all of San Diego, Calif.

[73] Assignee: Signal Pharmaceuticals, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/630,182

[22] Filed: Apr. 10, 1996

[51] Int. Cl.$^6$ .............................. C12Q 1/70; C12Q 1/68; C12N 5/10; C12N 15/63

[52] U.S. Cl. ............................... 435/5; 435/6; 435/240.2; 435/172.3; 435/235.1; 435/810

[58] Field of Search ............................... 435/6, 5, 240.2, 435/172.3, 235.1, 810

[56] References Cited

U.S. PATENT DOCUMENTS

| | | | |
|---|---|---|---|
| 5,168,062 | 12/1992 | Stinski | 435/240.2 |
| 5,418,132 | 5/1995 | Olivo | 435/5 |
| 5,591,579 | 1/1997 | Olivo | 435/6 |
| 5,776,502 | 7/1998 | Foulkes et al. | 424/617 |

FOREIGN PATENT DOCUMENTS

| | | |
|---|---|---|
| 336 626 A1 | 10/1989 | European Pat. Off. . |
| 521 427 A1 | 1/1993 | European Pat. Off. . |
| WO 92/12635 | 8/1992 | WIPO . |
| WO 93/01297 | 1/1993 | WIPO . |
| WO 94/00468 | 1/1994 | WIPO . |

OTHER PUBLICATIONS

Wilkinson, Diss Abst, vol. 51(2B), p. 568 (abstract cited), 1987.

Depto et al. J. of Virology 66: 3241–3246, 1992.

Shering et al, "Cell type specific expression in brain cell cultures from a short human cytomegalovirus major immediate early promoter depends on whether it is inserted into herpesvirus or adenovirus vectors", J. Gen. Virol. 78:445–459, 1997.

O'Hare et al, "Multiple trans–activating proteins of herpes simplex virus that have different target promoter specificities and exhibit both positive and negative regulatory functions", Cancer Cells 4:175–88 (Abstract only), 1986.

Stratagene catalog, p. 39, 1988.

Winkler et al., "UL69 of Human Cytomegalovirus, an Open Reading Frame with Homology to ICP27 of Herpes Simplex Virus, Encodes a Transactivator of Gene Expression," *Journal of Virology* 68(6): 3943–3954, 1994.

Depto and Stenberg, "Functional Analysis of the True Late Human Cytomegalovirus p. 28 Upstream Promoter: cis–Acting Elements and Viral trans–Acting Proteins Necessary for Promoter Activation," *Journal of Virology* 66(5): 3241–3246, 1992.

Gribaudo et al., "Interferons Inhibit Onset of Murine Cytomegalovirus Immediate–Early Gene Transcription," *Virology* 197: 303–311, 1993.

Kerry et al., "Identification of Sequence Elements in the Human Cytomegalovirus DNA Polymerase Gene Promoter Required for Activation by Viral Gene Products," *Journal of Virology* 68(7): 4167–4176, 1994.

Kohler et al., "Use of Recombinant Virus To Assess Human Cytomegalovirus Early and Late Promoters in the Context of the Viral Genome," *Journal of Virology* 68(10): 6589–6597, 1994.

Stinski and Roehr, "Activation of the Major Immediate Early Gene of Human Cytomegalovirus by cis–Acting Elements in the Promoter–Regulatory Sequence and by Virus–Specific trans–Acting Components," *Journal of Virology* 55(2): 431–441, 1985.

Klucher et al., "In Vivo and In Vitro Analysis of Transcriptional Activation Mediated by the Human Cytomegalovirus Major Immediate–Early Proteins," *Molecular and Cellular Biology* 13(2): 1238–1250, 1993.

Thrower et al., "Regulation of a Human Cytomegalovirus Immediate–Early Gene (US3) by a Silencer–Enhancer Combination," *Journal of Virology* 70(1): 91–100, 1996.

Depto and Stenberg, "Regulated Expression of the Human Cytomegalovirus p. 65 Gene: Octamer Sequence in the Promoter Is Required for Activation by Viral Gene Products," *Journal of Virology* 63(3): 1232–1238, 1989.

Arlt et al., "Identification of Binding Sites for the 86–Kilodalton IE2 Protein of Human Cytomegalovirus within an IE2–Reponsive Viral Early Promoter," *Journal of Virology* 68(7): 4117–4125, 1994.

Stasiak and Mocarski, "Transactivation of the Cytomegalovirus ICP36 Gene Promoter Requires the α Gene Product TRS1 in Addition to IE1 and IE2," *Journal of Virology* 66(2): 1050–1058, 1992.

Leach and Mocarski, "Regulation of Cytomegalovirus Late––Gene Expression: Differential Use of Three Start Sites in the Transcriptional Activation of ICP36 Gene Expression," *Journal of Virology* 63(4): 1783–1791, 1989.

Rüger et al., "Primary Structure and Transcription of the Genes Coding for the Two Virion Phosphoproteins p. 65 and p. 71 of Human Cytomegalovirus," *Journal of Virology* 61(2): 446–453, 1987.

*Primary Examiner*—Jeffrey Fredman
*Attorney, Agent, or Firm*—Seed and Berry LLP

[57] ABSTRACT

Cell lines and methods for detecting cytomegalovirus infection and identifying modulators of cytomegalovirus gene expression are disclosed. The cell lines carry an integrated plasmid that contains a reporter gene under the control of a cytomegalovirus promoter. Such cell lines may be used, for example, for specifically identifying HCMV infection in a biological sample.

8 Claims, 16 Drawing Sheets

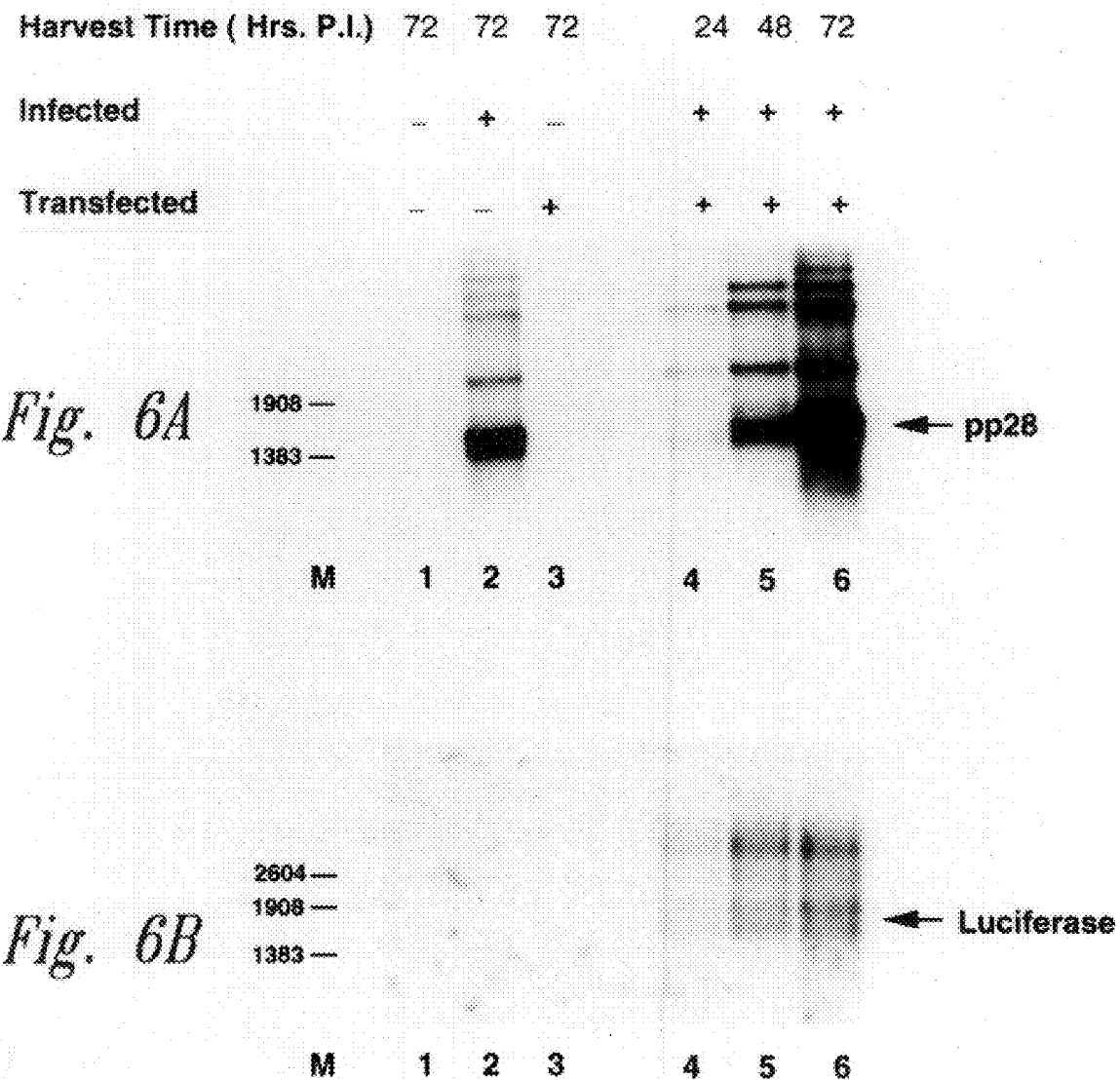

REPORTER CELL LINE SYSTEM FOR DETECTING CYTOMEGALOVIRUS AND IDENTIFYING MODULATORS OF VIRAL GENE EXPRESSION

TECHNICAL FIELD

The present invention relates generally to the detection of cytomegalovirus infection. The invention is more particularly related to cell lines useful for detecting cytomegalovirus in a sample and for identifying modulators of cytomegalovirus gene expression.

BACKGROUND OF THE INVENTION

Human cytomegalovirus (HCMV) is a ubiquitous member of the herpesvirus family that can induce a wide range of diseases, typically in newborns and immunocompromised adults. Nearly one percent of all live births in the United States are associated with congenital HCMV infection, with approximately 5 to 10 percent of infections resulting in significant neurological defects. In bone marrow transplant recipients, mortality due to HCMV pneumonia can be as high as forty percent. In addition, disseminated HCMV infection is common in immunocompromised patients, such as AIDS patients, and is frequently associated with conditions such as gastroenteritis and sight-threatening chorioretinitis.

The viral genome consists of a large double-stranded DNA molecule of approximately 230 base pairs packaged within an enveloped capsid to form the infectious virion. Productive infection is species and cell specific and requires the tightly coordinated expression of viral genes. This sequential viral gene expression is divided into three kinetic classes, immediate early (IE), early (E) and late (L). The IE gene products, which are located in four regions of the genome, are synthesized immediately after viral infection and rely primarily on host factors for their expression. The principle site of IE transcription, known as the major IE transcription unit, is in the large unique (UL) component of the genome (see, e.g., Thrower et al., *J. Virol.* 70:91–100, 1996; Klucher et al., *Mol. Cell. Biol.* 13:1238–1250, 1993; Arlt et al., *J. Virol.* 68:4117–4125, 1994). Early genes (such as the homolog for DNA polymerase) are transcribed prior to viral DNA replication (see, e.g., Ertl and Powell, *J. Virol.* 66:4126–4133, 1992; Stenberg et al., *J. Virol.* 63:2699–2708, 1989; He et al., *J. Virol.* 66:1098–1108, 1992) and the late genes, which constitute a majority of the viral genome are transcribed in abundance only after viral DNA replication (see, e.g., Depto and Stenberg, *J. Virol.* 66:3241–3246, 1992; Geballe et al., *J. Virol.* 57:864–874, 1986; Leach and Mocarski, J Virol. 63:1783–1791, 1989).

In order to successfully treat HCMV infection, sensitive and accurate diagnostic tests are required. Most current assays involve immunofluorescence techniques, which are cumbersome and often lack sensitivity. A more rapid cell-based assay is described in U.S. Pat. No. 5,418,132, but that assay is unable to distinguish among different herpesviruses. The development of diagnostic methods that detect HCMV infection rapidly and specifically would facilitate the diagnosis and treatment of HCMV infection.

In addition, conventional approaches to identifying inhibitors of viral gene expression, which typically involve the use of whole animals or tissues, are labor intensive and time consuming. Techniques involving plaque assays are more rapid, but still require on the order of two weeks for completion. A cell based viral assay has the potential for greater efficiency and sensitivity in the identification of useful therapeutic agents.

Accordingly, there is a need in the art for improved methods for diagnosing HCMV infection, and for identifying modulators of cytomegalovirus gene expression. The present invention fulfills these needs and further provides other related advantages.

SUMMARY OF THE INVENTION

Briefly stated, the present invention provides cell lines and methods for detecting cytomegalovirus (CMV) infection in a sample, and for identifying modulators of CMV gene expression. In one aspect, a method for detecting cytomegalovirus in a sample is provided, comprising: (a) contacting a sample with a cell, wherein the cell is stably transformed with a reporter gene operably linked to a cytomegalovirus promoter; and (b) determining a level of expression of the reporter gene, relative to a predetermined level in the absence of sample, and thereby detecting cytomegalovirus in the sample. In preferred embodiments, the cytomegalovirus promoter is selected from the group consisting of the major immediate early promoter, the pol promoter and the pp28 promoter.

In another aspect, the present invention provides a method for screening for a modulator of cytomegalovirus gene expression, comprising: (a) contacting a candidate modulator with a cell, wherein the cell is stably transformed with a reporter gene operably linked to a cytomegalovirus promoter; and (b) determining a level of reporter gene expression, relative to a predetermined level of expression in the absence of modulator, and therefrom evaluating the ability of the candidate modulator to inhibit or induce cytomegalovirus gene expression.

In yet another aspect, a kit for detecting cytomegalovirus in a sample is provided, comprising: (a) a cell line, wherein the cell line is stably transformed with a reporter gene operably linked to a cytomegalovirus promoter; and (b) a supply of reagents for detecting expression of the reporter gene.

In a further aspect, methods are provided for monitoring the effectiveness of a therapy for CMV infection, comprising: (a) exposing a patient infected with CMV to a candidate therapy; (b) contacting a sample obtained from the patient with a cell, wherein the cell is stably transformed with a reporter gene operably linked to a cytomegalovirus promoter; and (c) determining a level of expression of the reporter gene, relative to a predetermined level for cells contacted with a second sample obtained from the patient, wherein the second sample was obtained prior to the candidate therapy, and therefrom monitoring the effectiveness of the candidate therapy.

In still another aspect, the present invention provides methods for detecting a drug resistant CMV, comprising: (a) exposing a sample obtained from a patient infected with CMV to a drug; (b) contacting the sample with a cell, wherein the cell is stably transformed with a reporter gene operably linked to a cytomegalovirus promoter; and (c) determining a level of expression of the reporter gene, relative to a predetermined level for cells contacted with a second sample obtained from the patient, wherein the second sample is not exposed to the drug, and therefrom identifying a drug resistant CMV.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6, panels A and B, are an autoradiogram showing the results of a Northern blot analysis, using luciferase (panel B) and pp28 (panel A) gene fragments as probes, with mRNA isolated from uninfected, untransfected cells (lane 1), infected only cells (lane 2), transfected only cells (lane 3), and transfected, HCMV-infected cells 24 hours (lane 4), 48 hours (lane 5) and 72 hours (lane 6) post infection.

DETAILED DESCRIPTION OF THE INVENTION

As noted above, the present invention is generally directed to methods for detecting cytomegalovirus (CMV) infection in a sample, and for identifying modulators of CMV gene expression. The cytomegalovirus is preferably human cytomegalovirus (HCMV), but the present invention may also be applied to viruses that infect other hosts (e.g., murine cytomegalovirus or MCMV). Cell lines for use in such methods are also provided.

The cell lines of the present invention carry an integrated plasmid that contains a reporter gene under the control of a cytomegalovirus promoter. To prepare such a cell line, any cell type that is susceptible to infection by CMV may be transfected with an appropriate plasmid. Suitable cell types include, but are not limited to, human glial cells such as U373MG (see, e.g., Ripalti et al., *J. Virol.* 69:2047–2057, 1995) and U138MG (see, e.g., Wolff et al., *Virol.* 204:101–113, 1994), immortalized human fibroblasts, MDR-5 cells (human embryonic lung fibroblasts), human monocyte/macrophage cells (see, e.g., Fish et al., *J. Virol.* 70:1855–1862, 1996) and human endothelial cells. Stable transformation or transfection may be achieved by routine methods known to those of ordinary skill in the art, such as those described in Sambrook et al., *Molecular Cloning, A*

*Laboratory Manual,* Cold Spring Harbor Laboratories, Cold Spring Harbor, N.Y., 1989. Briefly, a plasmid containing a CMV promoter/reporter gene construct may be cotransfected with a vector carrying a selectable marker, such as the neomycin resistance gene (see, e.g., Wolff et al., *Gene* 130:167–173, 1993). Colonies of cells carrying the selectable marker may be isolated and assayed for expression of the reporter gene before and after viral infection. Cells transfected with the CMV promoter/reporter gene construct will show strong activation of reporter gene expression after infection with CMV. Following transfection, the cells may be maintained in a suitable selective medium, such as Dulbecco's Modified Eagle Media (DMEM) supplemented with 10% fetal bovine serum, 1% antimycotic/antibiotic and an appropriate compound for plasmid selection, such as G148.

Figure 1:
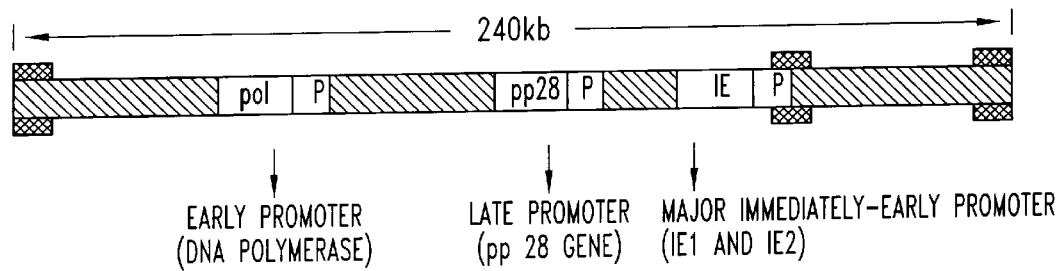
FIG. 1 is a diagram showing the location of the pol, pp28 and MIEP promoters within the HCMV genome.

Any CMV promoter that is capable of mediating expression of the reporter gene in the presence of CMV, but not in its absence, may be employed in the constructs of the present invention. Promoters employed in the constructs of the present invention should not cause constitutive expression of the reporter gene in the absence of CMV. Suitable promoters include, but are not limited to, the immediate early (IE or α) promoters UL122–123 (MEP), UL36–38, UL3, US3 and TRS1 (US22 family); the early (E or β) promoters UL54 (pol), UL44 (ICP36, p52), UL122, UL84 and UL98; and the late (L or γ) promoters UL99 (pp28), gH (UL75) and IE40. These promoters are described, for example, in Thrower et al., *J. Virol.* 70:91–100, 1996; Pari et al., *Antimicrobial Agents and Chemotherapy* 39:1157–1161, 1995; Geballe et al., *J Virol.* 57:864–874, 1986; Leach and Mocarski, *J. Virol.* 63:1783–1791, 1989; Pari et al., *J Virol.* 67:2575–2582, 1993; Ertl and Powell, *J. Virol.* 66:4126–4133, 1992; Stasiak and Mocarski, *J. Virol.* 66:1050–1058, 1992; Meyer et al., *J. Virol.* 62:2243–2250, 1988; Stenberg et al., *J. Virol.* 63:2699–2708, 1989; Ruger et al., *J. Virol.* 61:446–453, 1987; Klucher et al., *Mol. Cell. Biol.* 13:1238–1250, 1993; Arlt et al., *J. Virol.* 68:4117–4125, 1994; Lang et al., *J. Virol.* 69:6030–6037, 1995; Spector and Tevethia, *J. Virol.* 68:7549–7553, 1994; He et al., *J. Virol.* 66:1098–1108, 1992; Depto and Stenberg, *J. Virol.* 63:1232–1238, 1989; Adam et al., *J. Virol.* 69:5304–5310, 1995. Preferred promoters are those that do not permit significant reporter gene expression in the presence of other herpes viruses, such as HSV-1. Such promoters include the major immediate-early promoter (MIEP) (described, for example, in Kohler et al., *J. Virol.* 68:6589–6597, 1994), the pol promoter (described, for example, in Kerry et al., *J. Virol.* 68:4167–4176, 1994) and the pp28 promoter (described, for example, in Depto and Stenberg, *J. Virol.* 66:3241–3246, 1992). The location of these promoters within the HCMV genome is provided in FIG. 1.

The reporter gene may be any gene whose product can serve as a marker for the detection of gene expression. Many such reporter genes are known to those of ordinary skill in the art. Several reporter genes have been used extensively: bacterial chloramphenicol acetyl transferase (CAT), firefly luciferase (LUC), human growth hormone (hGH), alkaline phosphatase and bacterial β-galactosidase. Both cat and luc genes are most commonly used in eukaryotic cells, and luc is a particularly preferred reporter gene. Luciferase assays offer the advantages of being 10–1000 fold more sensitive than CAT assays, negligible background, fast quantitation and short half-life (3 h for luc compared to 50 h for CAT in mammalian cells). These properties of the luciferase reporter gene provide a more sensitive monitor of changes in transcription than the more stable reporters like CAT in stable cell line (see, e.g., Moriera et al., *Methods in Mol. and Cell. Biol.* 3:23–29, 1992).

The promoter/reporter gene construct may then be inserted into an appropriate expression vector using techniques well known to those of ordinary skill in the art. Suitable expression vectors include the pGL2-Basic Plasmid (Promega, Madison, Wis.).

The cell lines described above may be used to detect CMV infection in any fluid sample, and preferably in a biological sample obtained from a warm-blooded animal. More preferably, the sample is a human biological sample including, but not limited to, urine, throat secretions, genital secretions, breast milk and blood. A fluid sample may also be prepared from a solid material by extraction or other procedures common in the art. It will be evident to those of ordinary skill in the art that one or more preparatory steps, such as centrifugation, may be desirable to place a sample in optimal condition for testing. Other viruses may also be present in the fluid sample, including herpes simplex virus-1 and -2 (HSV-1 and -2), human herpesvirus 6 (HHV6), Varicella-zoster virus (VZV), Epstein-Barr virus (EBV), adenovirus and RNA viruses such as influenza, rhinovirus and respiratory syncytial virus (RSV).

To determine whether a sample contains CMV, the sample is contacted with a cell that carries an integrated plasmid containing a reporter gene operably linked to a cytomegalovirus promoter, as described above. The sample and cell are typically combined and allowed to incubate for a period of time and under conditions sufficient to achieve viral infection of the cell. For example, $30 \times 10^3$ cells per well may be seeded into a 96 well plate in an appropriate selection medium and combined with about 10–50 µl of sample. The sample and cells are then typically incubated for about 2 to 5 days, and preferably for about 48 hours.

Following incubation, the level of expression of the reporter gene is determined using a technique appropriate for the particular reporter protein. In many cases, the reporter protein is an enzyme capable of detection by routine calorimetric, fluorimetric or luminometric techniques. For example, luciferase activity may be detected using standard luminometric methods, with luciferin as the enzyme substrate (de-Wet et al., *Mol. Cell. Biol.* 7:725–737, 1987). Appropriate methods for detecting the level of expression of other reporter genes will be apparent to those of ordinary skill in the art and may be found, for example, in Sambrook et al., *Molecular Cloning: A Laboratory Manual,* Cold Spring Harbor Laboratories, Cold Spring Harbor, N.Y., 1989 and in manufacturer's protocols.

To determine the presence or absence of CMV in the sample, the signal detected in the reporter protein assay is generally compared to a signal that corresponds to a predetermined cut-off value. This cut-off value is preferably the average mean signal obtained from cells incubated in the absence of a CMV-infected sample. In general, a sample generating a signal that is approximately two-fold above the mean is considered positive for CMV infection. The above assay may also be used to determine the amount of CMV in a sample. Absolute levels of CMV may be obtained by comparing the signal generated by a sample with the signal generated by standards having known amounts of the virus, using techniques well known to those of ordinary skill in the art. As discussed in more detail below, the determination of relative levels of CMV may also be useful in, for example, monitoring a therapy for CMV infection or evaluating the response of a CMV isolate to a given drug (e.g., in identifying drug resistance).

A significant advantage of the detection method described above is the ability to specifically detect CMV. It has been found within the context of the present invention that the use of certain promoters (such as MIEP, pol and pp28), render the above method sensitive for the detection of CMV without detecting HSV-1. This unexpected specificity allows the precise identification of CMV, which in turn permits the use of treatments precisely tailored to the particular virus.

Detection of CMV by the method described above may also be useful for identifying drug-resistant CMVs and for monitoring therapy. In these aspects, the change in the level of CMV in response to exposure to a drug or other therapy is evaluated. To evaluate whether a CMV is resistant to a given drug, a sample containing the virus is exposed to a suitable amount of the drug, using methods appropriate for the sample type which will be apparent to those of ordinary skill in the art. Following exposure, the sample is then tested for CMV as described above. If the CMV in the treated sample is resistant to the particular drug, CMV will be detected. It should be noted that the level of drug resistant CMV that is detected in the sample may temporarily decrease in response to treatment. Nonetheless, the CMV is considered drug resistant if either the readout value doesn't change after two-four weeks of treatment, or the readout value initially decreases after two-three weeks of treatment and thereafter increases at a follow-up evaluation.

To evaluate the effectiveness of a therapy for CMV infection, suitable samples obtained from one or more infected patients are first evaluated for CMV as described above. The candidate therapy is then applied to the patient(s) and the level of CMV following treatment is determined. For example, blood drawn from an infected patient may be tested for the presence of CMV prior to treatment. After 2–4 weeks of treatment, a second blood sample may be drawn and tested for CMV. A therapy is considered effective if the therapy lowers the level of CMV by at least two-fold. Once a therapy is found to be effective, further treatment of patients may be monitored by performing similar CMV assays at intervals of about 2–4 weeks until CMV is no longer detectable.

Figure 2A:
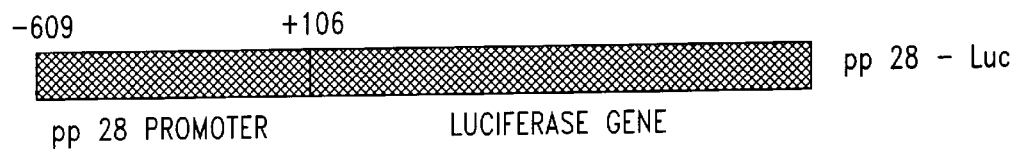
FIG. 2 is a diagram illustrating representative CMV promoter/reporter gene constructs (pp28-luc, pol-luc and MIEP-luc).
Figure 2B:
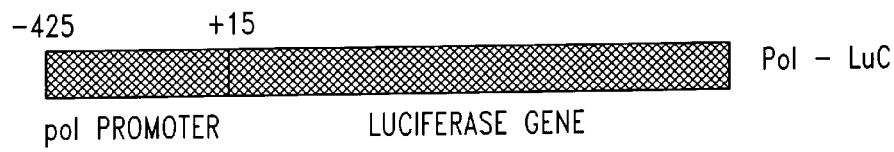
Figure 2C:
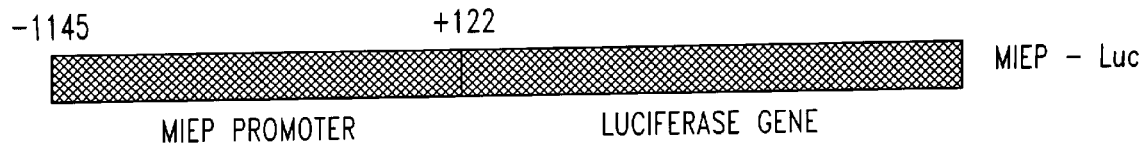

In a related aspect of the present invention, diagnostic kits are provided for detecting the presence of CMV. Such kits generally comprise transfected cells, as described above and, in a separate container, a supply of reagents sufficient to allow detection of reporter gene expression. For example, kits may comprise cells that contain an expression vector with a luciferase gene operably linked to the MIEP, pol or pp28 promoter, as shown in FIG. 2. In such a kit, the accompanying supply of reagents would be sufficient to allow the detection of luciferase activity. Suitable kits are available from Promega (Madison, Wis.) and Analytical Luminescence Laboratories, (San Diego, Calif.). Kits comprising other constructs and reagents for use in detecting other reporter proteins may be similarly prepared.

It has been found, within the context of the present invention, that the reporter genes in the transfected cells are regulated similarly to the endogenous viral genes. Accordingly, in yet another aspect, the present invention provides a method for identifying modulators of CMV gene expression, using cells stably transfected as described above. Within the context of the subject invention, a "modulator" is any compound that is capable of inducing or inhibiting CMV gene expression. A modulator may act directly to induce or inhibit viral gene transcription or translation. Alternatively, a modulator may affect viral DNA replication.

Modulators may be identified using a variety of assay formats. One preferred format is a high throughput screen that permits the simultaneous testing of a large number of candidate modulators. For example, cells containing the luc gene may be seeded in 96-well plates ($3 \times 10^4$ cells per well) and incubated for about 18 hours in a 37° C. humidified environment. Candidate modulators may then be added to a final concentration of 10 μg/mL, and the plates incubated for 30 minutes at 37° C. HCMV may then be added at 2–5 μl/cell. Forty-eight hours after infection, the cells are washed and lysed. An aliquot of lysate is then transferred to a black 96-well plate and luciferase assay reagent is added. Luciferase activity (luminescence) in each well is then measured. It will be apparent to those of ordinary skill in the art that some modification of this protocol may be appropriate when other reporter genes are used. In addition, cell-specific staining may be employed for the detection of reporter gene expression.

Regardless of the assay format, the signal obtained from cells incubated with candidate modulator and virus is generally compared to a signal that corresponds to a predetermined cut-off value. This cut-off value is preferably the average mean signal obtained from cells incubated in the presence of virus, but in the absence of modulator. In general, a candidate modulator generating a signal that is one-fold or greater above the mean is considered to be an inducer of CMV gene expression, and a candidate modulator generating a signal that is approximately 25%, preferably greater than 50% below the mean is considered to be an inhibitor of CMV gene expression.

Modulators that inhibit CMV gene expression have therapeutic potential as antiviral agents. In particular, such modulators may find use in the treatment of HCMV-associated diseases such as pneumonia, gastroenteritis and chorioretinitis. Further characterization of modulators may be achieved, using the assay described above, by comparing CMV levels in patient samples obtained prior to treatment with a modulator with the levels in samples obtained at various times following treatment.

The following Examples are offered by way of illustration and not by way of limitation.

EXAMPLES

Example 1

Preparation of Transfected Cells

This Example illustrates the preparation of cell lines carrying an integrated plasmid that contains a reporter gene under the control of a cytomegalovirus promoter.

A. Plasmid Construction

1. MIEP-luc

The MIEP promoter sequence, from position −1145 to +122, was amplified by PCR using plasmid PSE (Peter Ghazal, The Scripps research Institute) as a template. The primers are: 5'-CGGGGTACCGCTGCAGTGAATAATAAAATG-3' SEQ ID NO:1 (sense primer), and 5'CGGGGTACCGTCACTCTTGGCACGGGGAATC-3' SEQ ID NO:2 (antisense primer). These oligo primers introduced a KpnI restriction site at the 5' and 3' end of MIEP promoter fragment. The KpnI digested PCR fragment was inserted into KpnI digested pGL2-basic luciferase reporter plasmid (Promega, Madison, Wis.). The promoter direction was determined and PCR fidelity of the promoter sequence was confirmed by sequencing.

2. Pol-luc

The Pol promoter sequence, from position −425 to +15, was amplified by PCR using cosmid pCM1058 (Peter Ghazal) as template. The primers are: 5'-CCCAAGCTTGGGGAATTCAACTCGTACAAGCAG-3' SEQ ID NO:3 (sense primer), and 5'CCCAAGCTTGGGTCAGACGACGGTGGTCCC-3' SEQ ID NO:4 (antisense primer). These oligo primers introduced a HindIII restriction site at the 5' and 3' end of Pol promoter fragment. The HindIII digested PCR fragment was inserted into HindIII digested pGL2-basic luciferase reporter plasmid (Promega, Madison, Wis.). The promoter direction was determined and PCR fidelity of the promoter sequence was confirmed by sequencing.

3. pp28-luc

The pp28 promoter sequence, from position −609 to +106, was amplified by PCR using cosmid PCM1 (Peter Ghazal, Scripps Research Institute) as a template. The oligonucleotide primer sequences are:

5'-AAAGGTACCGCCGGCGTCTCGCCGGGCATC-3' SEQ ID NO:5 (sense primer), and

5'-AAAAAGCTTGCCGGCCCAGCAGCTCGGGCG-3' SEQ ID NO:6 (antisense primer).

These oligonucleotides primers introduced a KpnI restriction site at the 5'-end and a HindIII site at the 3'-end of the pp28 promoter fragment. Unique sites, KpnI and HindIII allowed directional cloning into the pGL2-basic luciferase reporter plasmid (Promega, Madison, Wis.), resulting in the pp28-luc promoter construct shown in FIG. 2. The PCR fidelity of the pp28 promoter sequence was confirmed by sequencing.

B. Establishment of Stable Cell Lines

The HCMV permissive human glioblastoma cell line U373 MG was transfected with the constructs described above. Conditions for cell growth were as described in Baracchini et al., *Virol.* 188:518–529, 1992. The pp28-luciferase reporter and pSV2Neo selection plasmid were cotransfected into U373 MG cells by the calcium phosphate method. Transfectants were selected in medium containing 0.6 mg/ml G418 on the third day after transfection. G418-resistant clones were expanded and 3×10$^4$ cells seeded in triplicate in a 96 well plate.

Cells were infected with HCMV (Towne strain, obtained from American Type Culture Collection, Rockville, Md.) at 5–10 pfu/cell. 48 hours postinfection, cells were harvested and assayed for luciferase activity as follows. Culture media was removed and the cells were rinsed once with PBS buffer without Ca$^{++}$ and Mg$^{++}$(137 mM NaCl, 2.7 mM KCl, 4.3 mM Na$_2$HPO$_4$ and 1.4 mM KH$_2$PO$_4$). Sixty microliters of 1X Lysis buffer containing 25 mM Tris-phosphate, pH 7.8, 2 mM DTT, 2 mM 1,2-diaminocyclohexane-N,N,N',N'-tetraacetic acid, 10% glycerol and 1% Triton X-100 (Promega Cell Culture Lysis Buffer, Madison, Wis.) was added. After incubation at room temperature for 15 minutes, 40 μL of cell lysate was transferred to a black 96-well plate and 50 μL of luciferase substrate (Promega, Madison, Wis.) was added to each well. Plates were read immediately in a Packard TopCount™ (Packard, Hartford, Conn.). Clones showing high luciferase inducibility were further analyzed by PCR to ascertain the integrity of the reporter transcriptional unit integrated into the genomic DNA.

Example 2

Analysis of Reporter Gene Expression upon Viral Infection

This Example illustrates the kinetic analysis of reporter gene expression, using the cell lines prepared in Example 1, upon HCMV infection.

Figure 3:
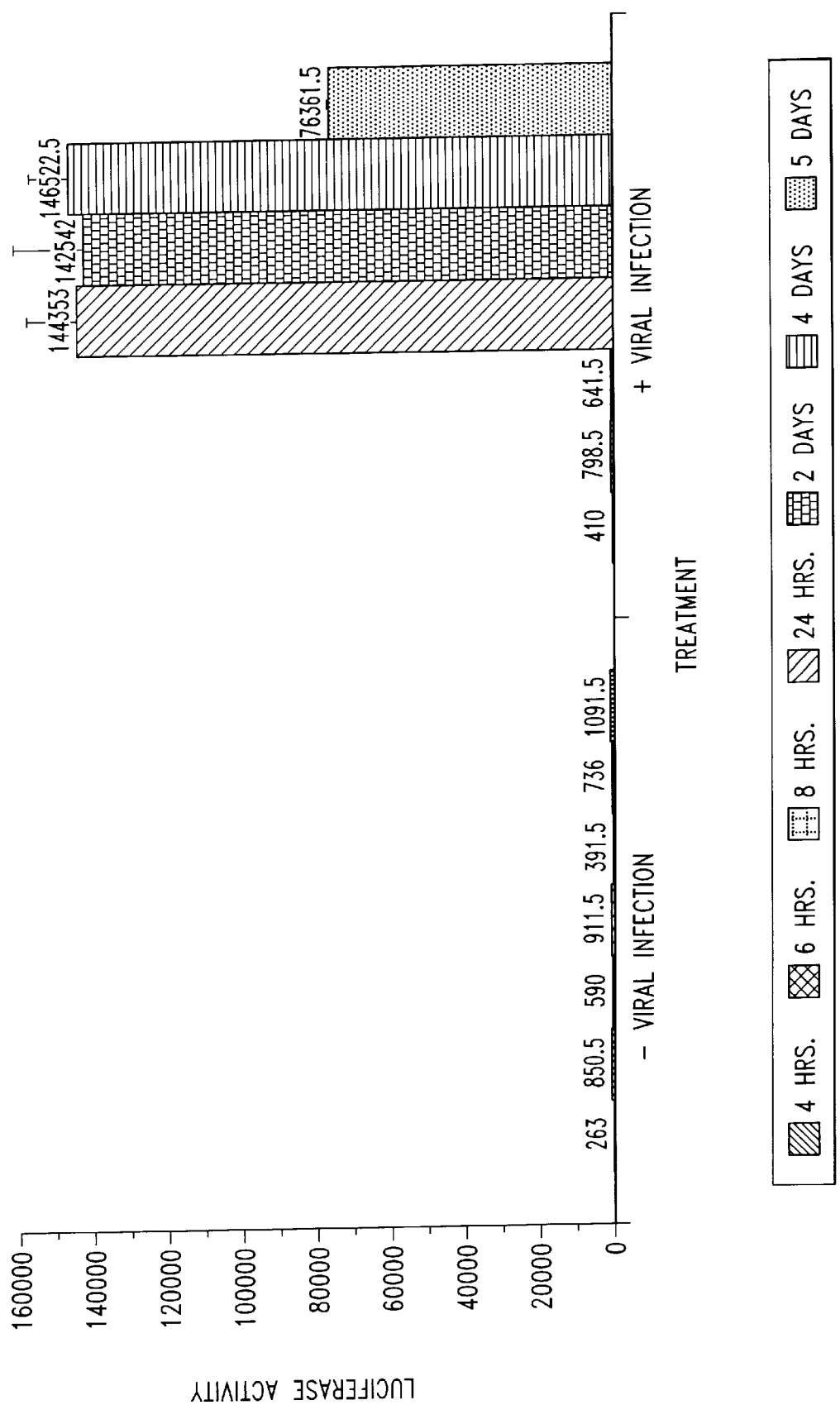
FIG. 3 is a graph presenting the results of a kinetic analysis of luciferase induction upon viral infection in the representative MIEP-luc stable cell line. Luciferase activity is shown at 4 hours, 6 hours, 8 hours, 24 hours, 2 days, 4 days and 5 days, with (columns 8–14) and without (columns 1–7) HCMV infection.
Figure 4:
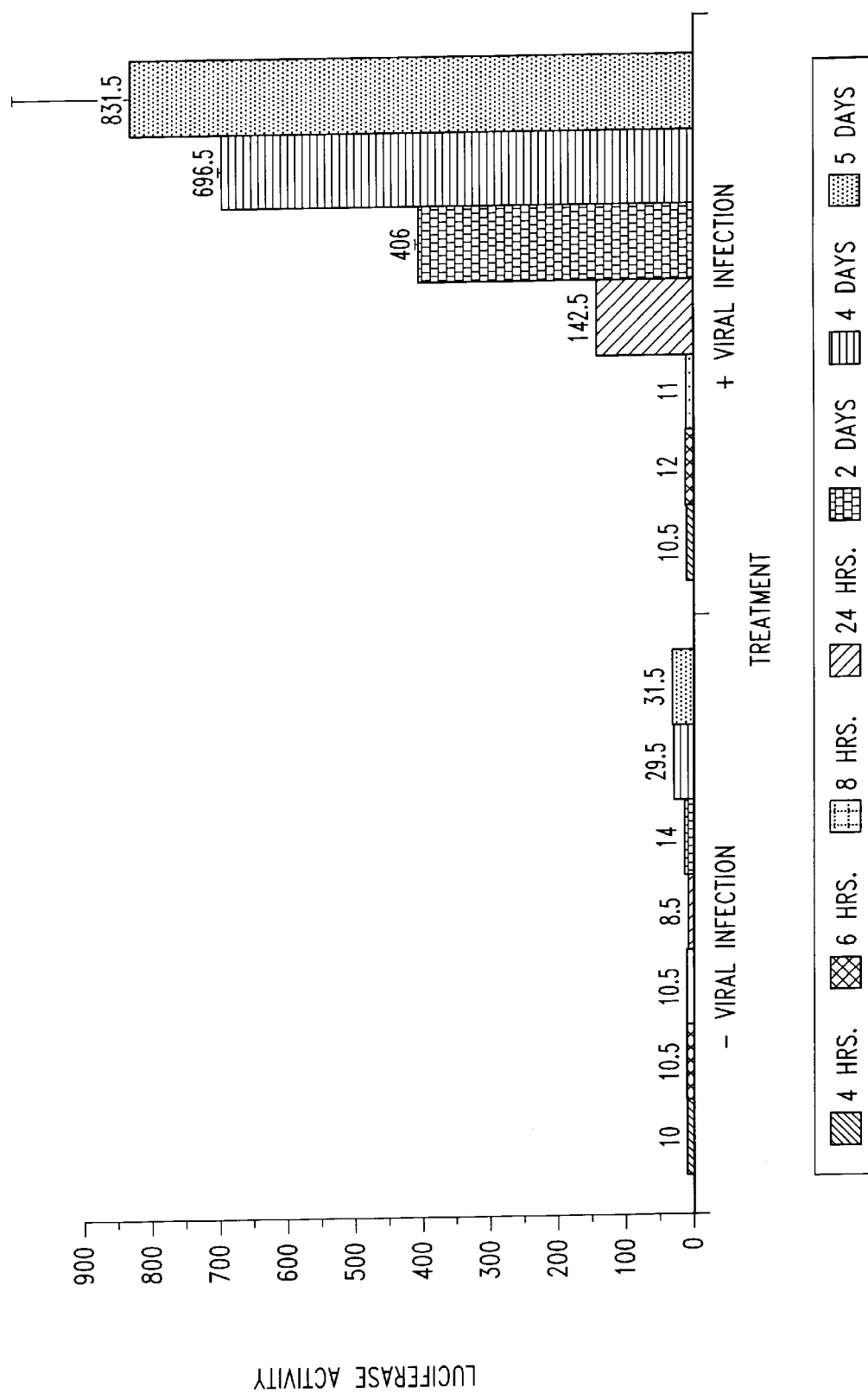
FIG. 4 is a graph presenting the results of a kinetic analysis of luciferase induction upon viral infection in the representative pol-luc stable cell line. Luciferase activity is shown at 4 hours, 6 hours, 8 hours, 24 hours, 2 days, 4 days and 5 days, with (columns 8–14) and without (columns 1–7) HCMV infection.
Figure 5:
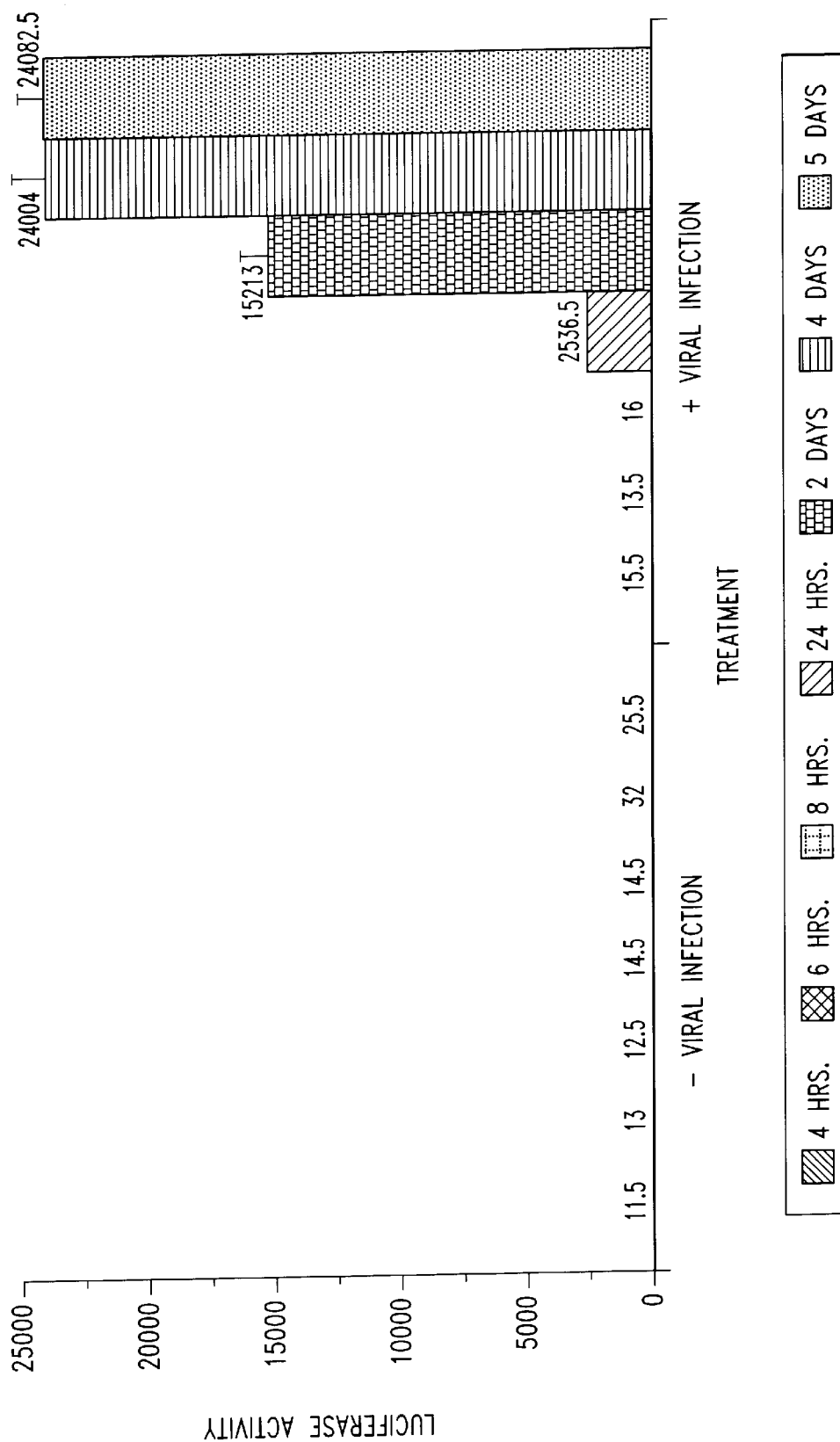
FIG. 5 is a graph presenting the results of a kinetic analysis of luciferase induction upon viral infection in the representative pp28-luc stable cell line. Luciferase activity is shown at 4 hours, 6 hours, 8 hours, 24 hours, 2 days, 4 days and 5 days, with (columns 8–14) and without (columns 1–7) HCMV infection.

Cell lines prepared as described above were infected with the Towne strain of HCMV (ATCC Accession No. VR-977) at a multiplicity of infection of 5–10 pfu/cell, and luciferase activity was measured at various times over a period of 5 days. The results are presented in FIGS. 3–5. For each cell line, luciferase activity was detected at 24 hours. The MIEP-luc cell line showed maximal activity at 24 hours–4 days, with decreased activity at 5 days post-infection (FIG. 3). The pol-luc (FIG. 4) and pp28 (FIG. 5) cell lines showed a gradual increase at 48 hours, peaking at 4–5 days postinfection. In each case, the kinetics of gene expression were similar to that expected for the endogenous viral gene.

These data indicate that luciferase expression regulated through the HCMV promoter tested is very low in permissive cells but is strongly activated upon viral infection. However, if the transfected cells were infected with the UV-treated virus, luciferase activity was not detected (data not shown). Due to the short half-life of luciferase we concluded that the increase in luciferase activity reflects activation of transcription and not simply accumulation of the reporter protein. These results indicate that activation of these promoters required viral gene expression, and that the promoters respond to viral infection similarly to promoters within the context of the viral genome.

The expression patterns for the pp28-luc gene and the endogenous pp28 gene were also compared using Northern blot analysis, with luciferase and pp28 gene fragments as probes (FIG. 6). Transfected and infected U373 MG cells were processed for messenger RNA as indicated by the manufacturer (Stratagene, La Jolla, Calif.), and equal aliquots of MRNA were subjected to Northern blot analysis. Probes were labeled with α-$^{32}$P-dCTP (3000 Ci/mmol, Amersham, Arlington Heights, Ill.) using Prime-It RmT random primer labeling kit (Stratagene, La Jolla, Calif.). Blots were hybridized to the radiolabeled probes for each gene using a QuikHyb hybridization solution following the manufacturers protocol (Stratagene, La Jolla, Calif.).

This analysis showed that pp28 MRNA was detectable at 24 hours and increased at 48 and 72 hours progressively (FIG. 6, panel A, lanes 4, 5, and 6, respectively). In contrast, no luciferase MRNA could be detected in cells infected only (FIG. 6, panel B, lane 2), or transfected only (FIG. 6, panel B, lane 3) compared to mock-treated control cells (FIG. 6, panels A and B, lane 1). These results suggest that the pp28 promoter, out of the viral genome context, behaves similarly to its endogenous counterpart.

Figure 7A:
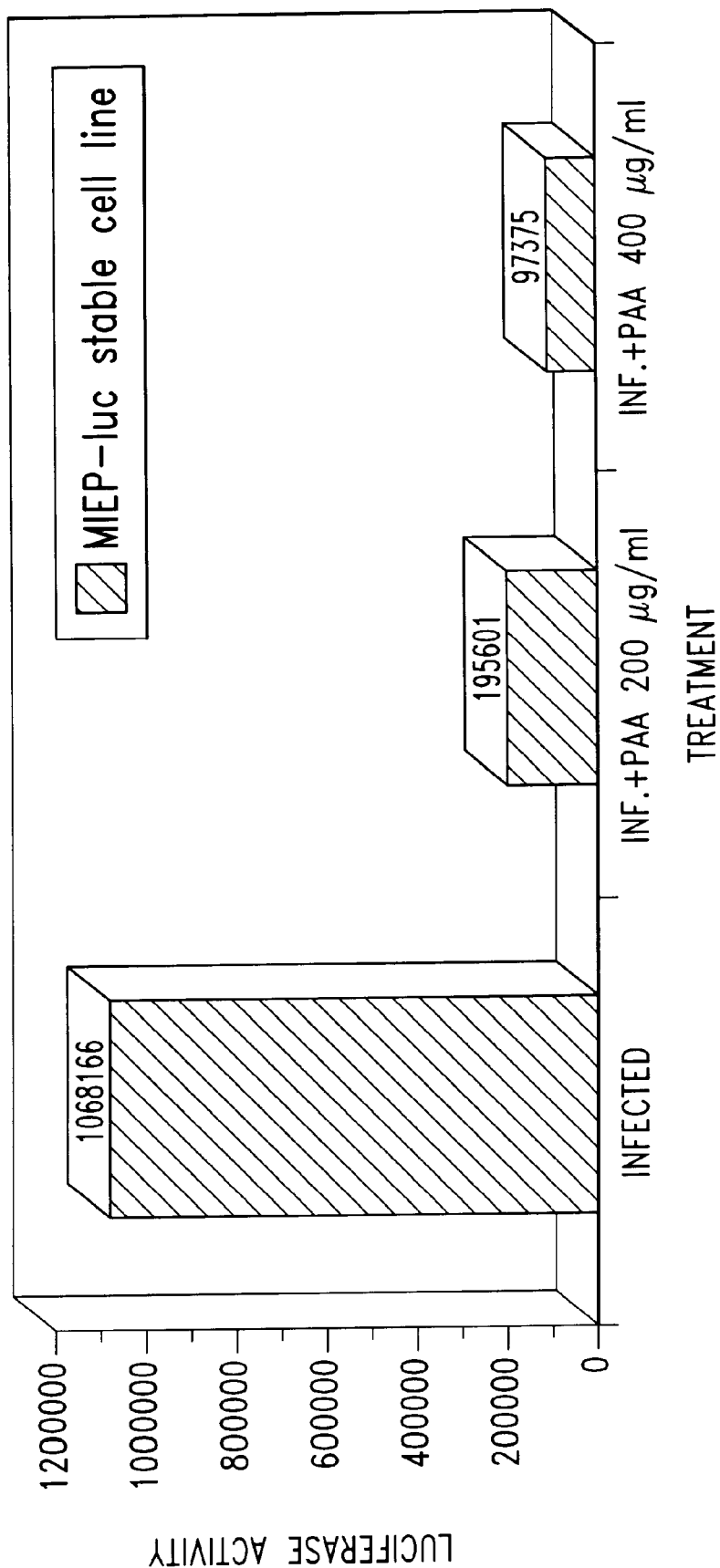
FIG. 7, panel A, is a graph depicting the luciferase activity detected in MIEP-luc cells 48 hours after infection with HCMV in the absence of viral DNA replication inhibitor (column 1), in the presence of 200 μm phosphonoacetic acid (column 2) and in the presence of 400 μg/mL phosphonoacetic acid (column 3). Panel B is an autoradiogram showing the results of a Northern analysis using mRNA prepared from MEP-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, IE-specific mRNA and beta-actin mRNA as indicated by the arrows. Panel C is an autoradiogram showing the results of a Western analysis using protein lysates prepared from MIEP-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase and IE proteins, as indicated by the arrows.
Figure 7B:
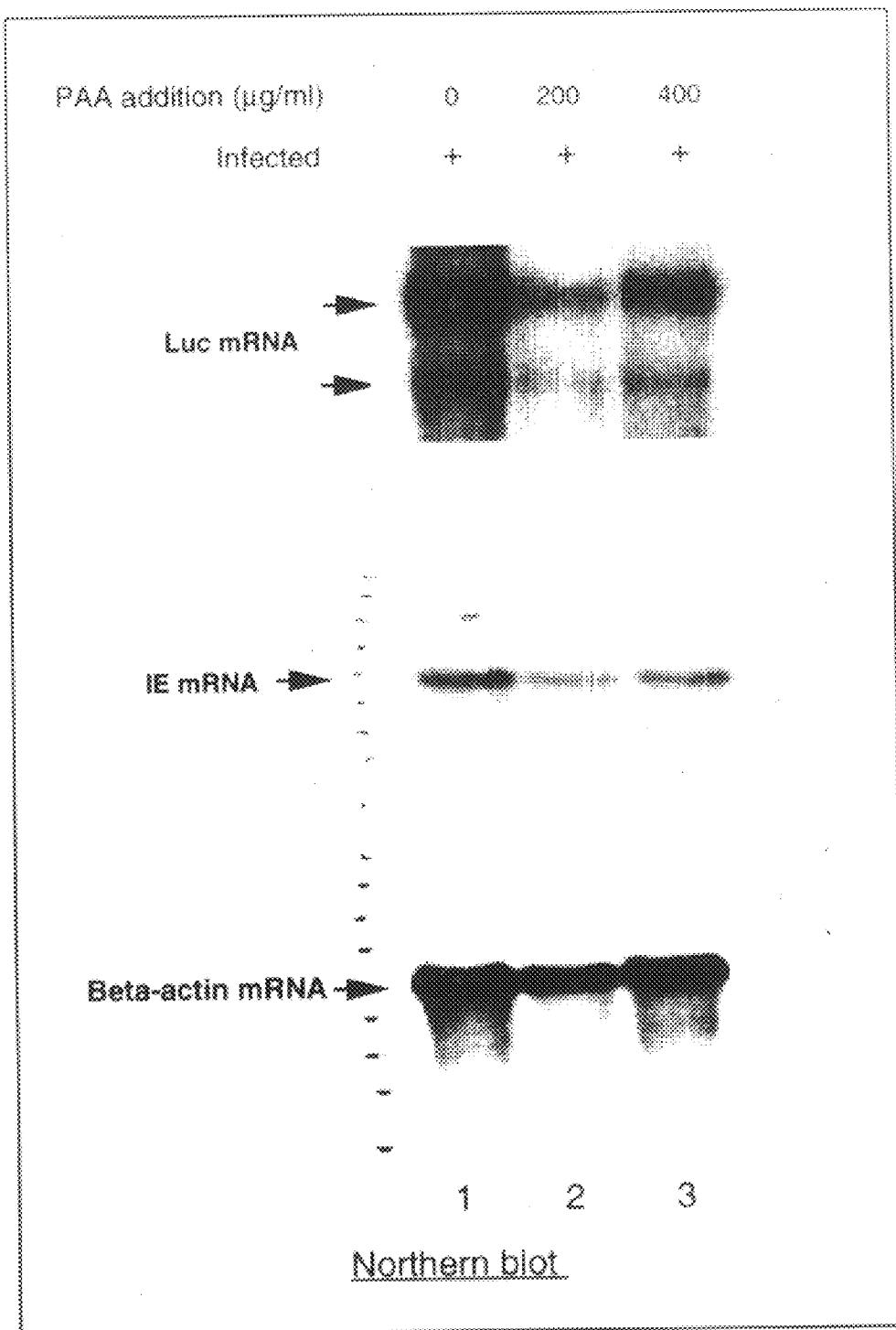
Figure 7C:
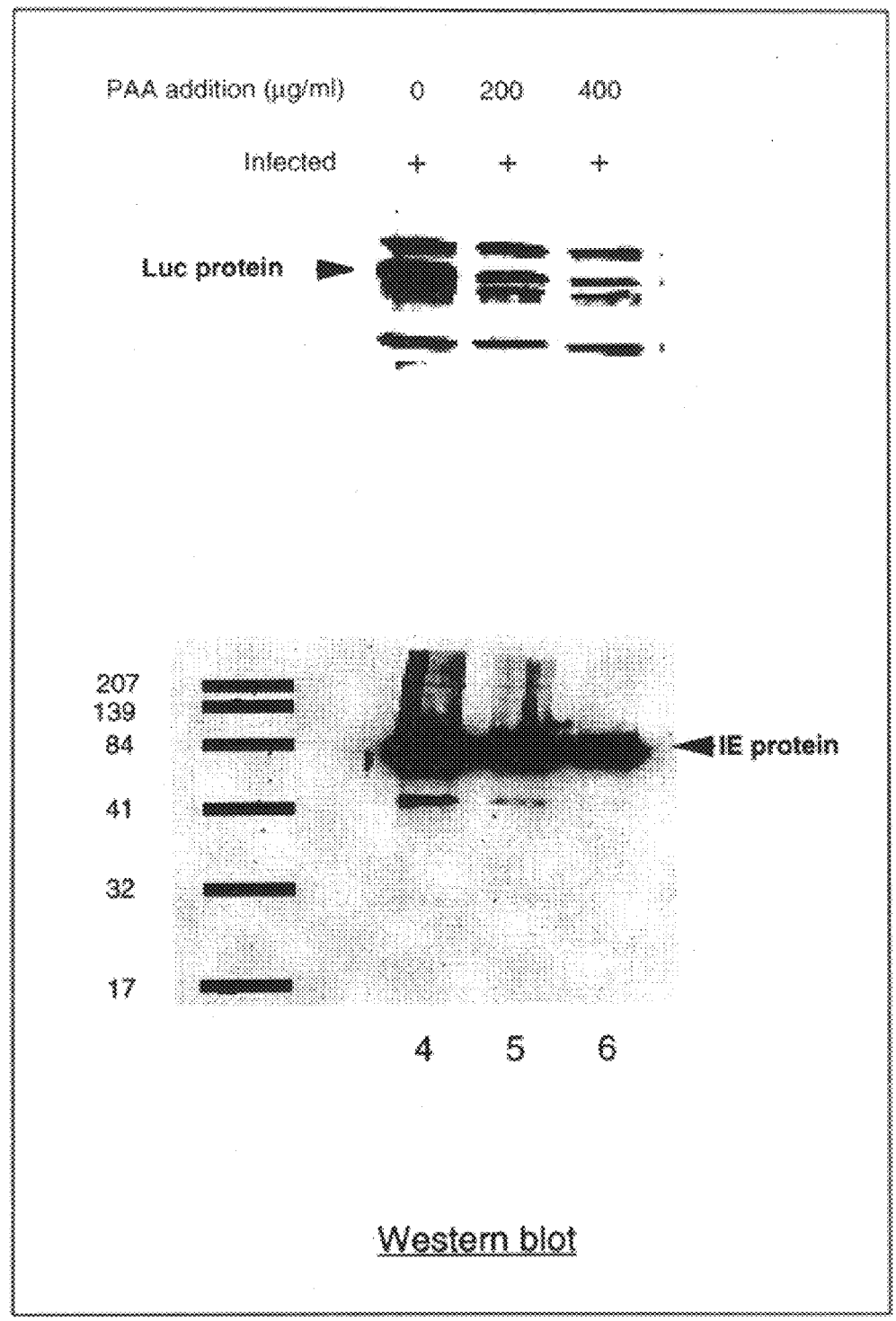
Figure 8A:
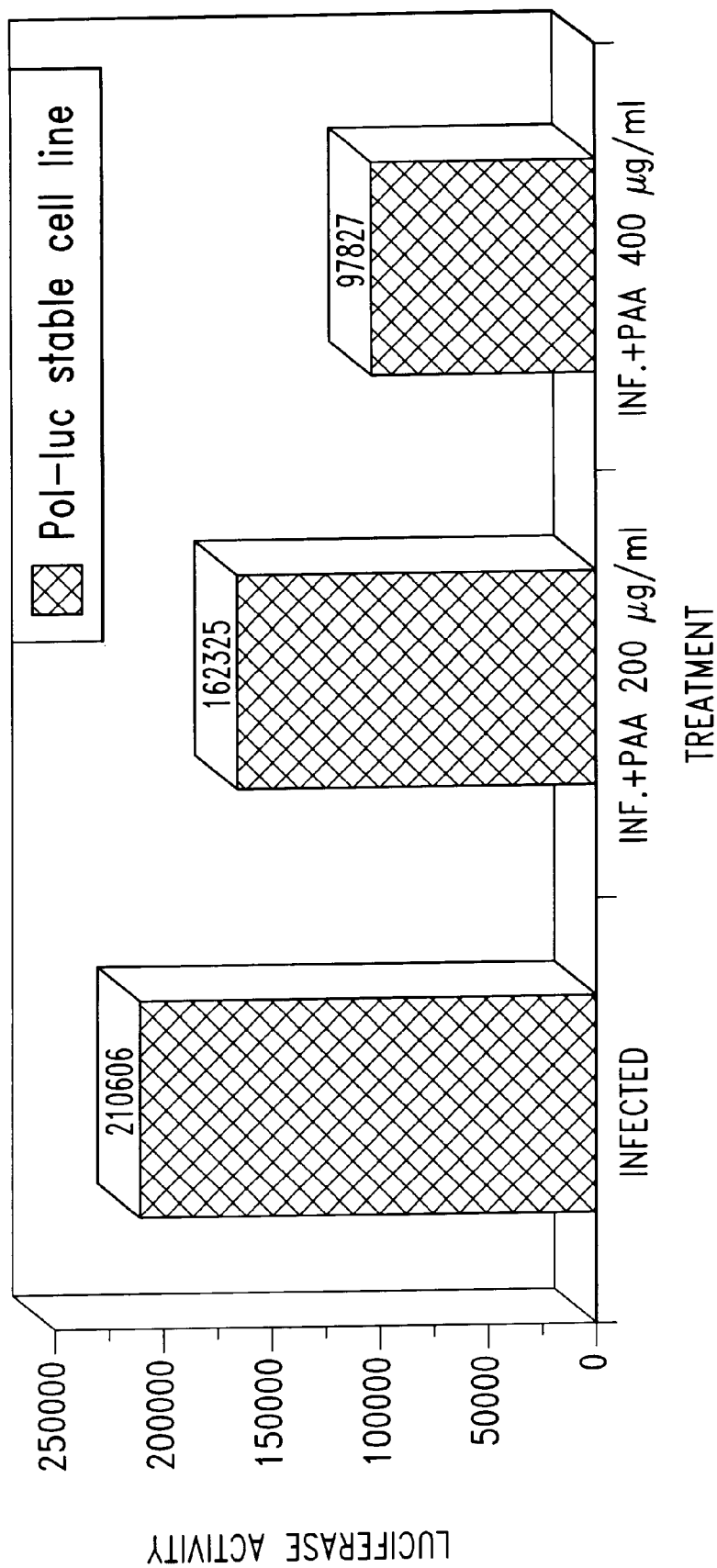
FIG. 8, panel A, is a graph depicting the luciferase activity detected in pol-luc cells 48 hours after infection with HCMV in the absence of viral DNA replication inhibitor (column 1), in the presence of 200 μg/mL phosphonoacetic acid (column 2) and in the presence of 400 μg/mL phosphonoacetic acid (column 3). Panel B is an autoradiogram showing the results of a Northern analysis using mRNA prepared from pol-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, pol specific mRNA and beta-actin mRNA as indicated by the arrows. Panel C is an autoradiogram showing the results of a Western analysis using protein lysates prepared from pol-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase, as indicated by the arrow.
Figure 8B:
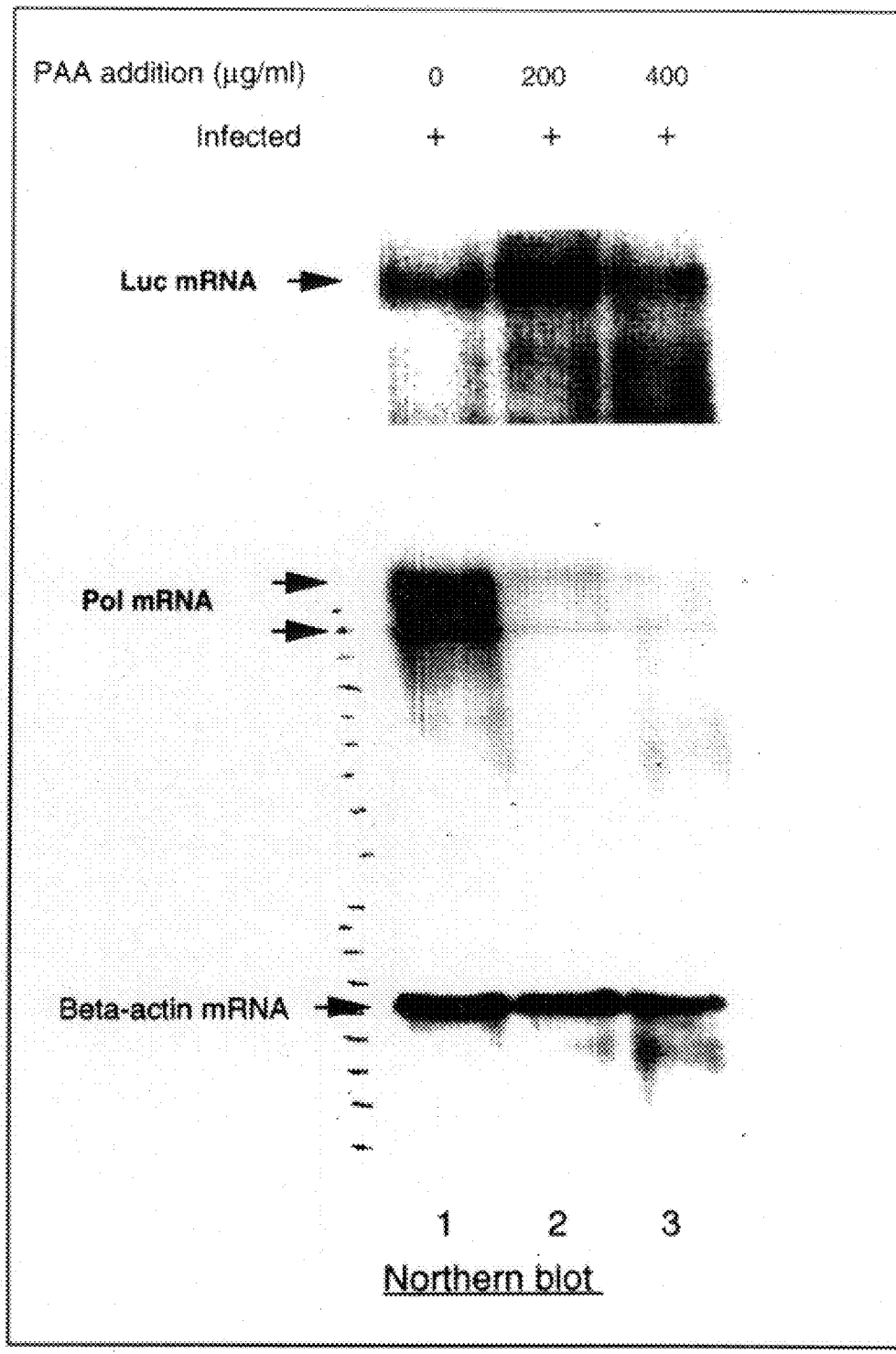
Figure 8C:
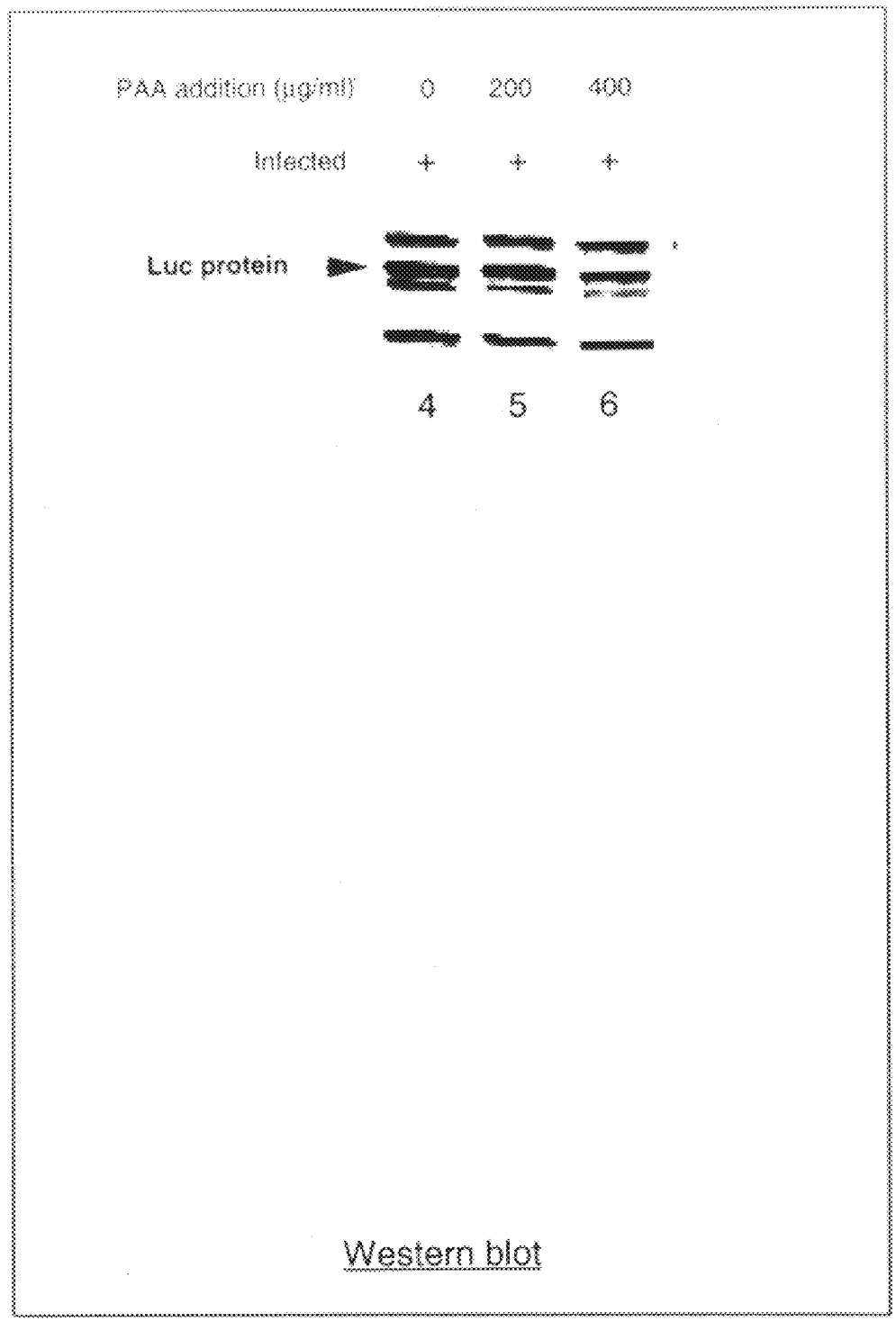
Figure 9A:
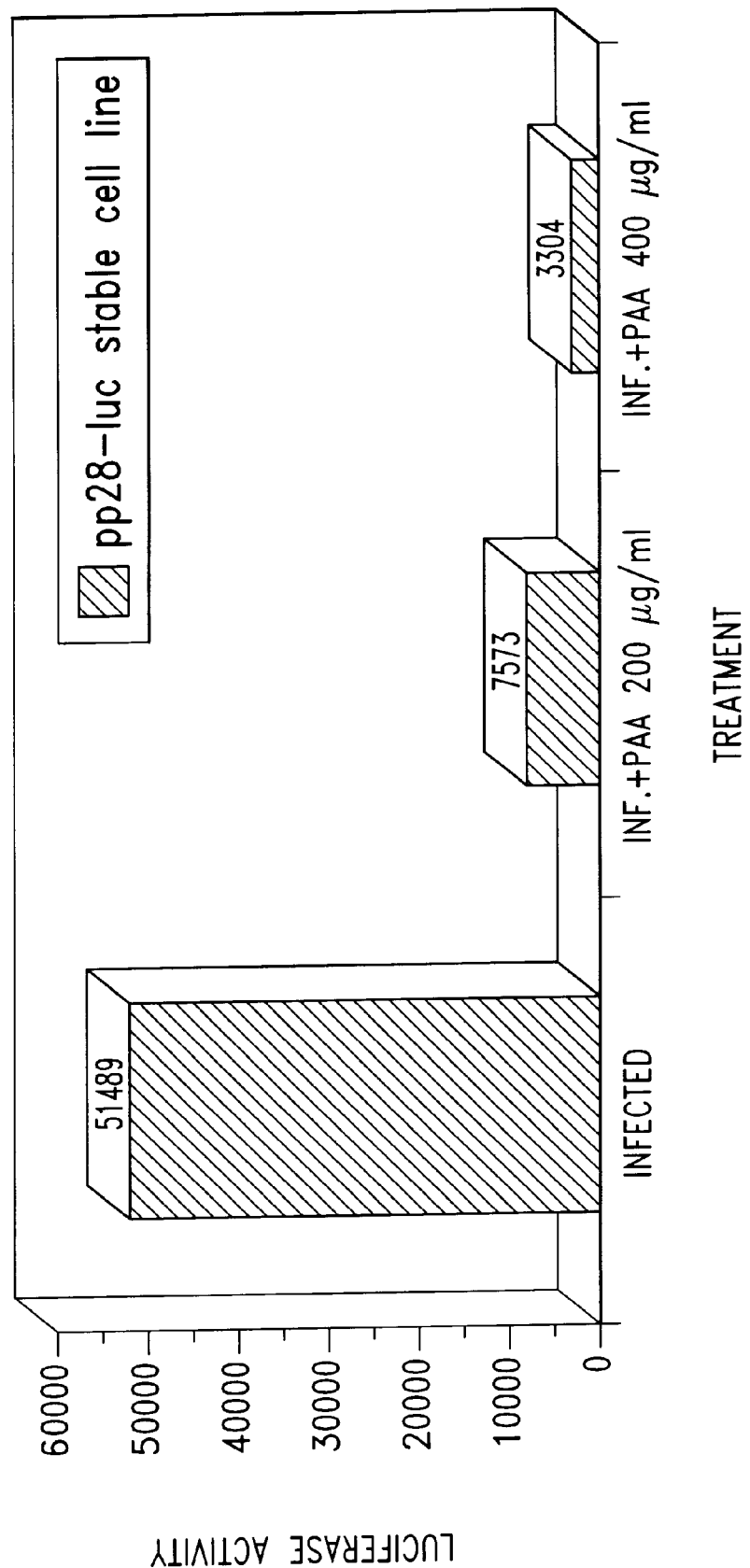
FIG. 9, panel A, is a graph depicting the luciferase activity detected in pp28-luc cells 48 hours after infection with HCMV in the absence of viral DNA replication inhibitor (column 1), in the presence of 200 μg/mL phosphonoacetic acid (column 2) and in the presence of 400 μg/mL phosphonoacetic acid (column 3). Panel B is an autoradiogram showing the results of a Northern analysis using mRNA prepared from pp28-luc cells 48 hours after infection with HCMV in the absence of viral DNA replication inhibitor (lane 1), in the presence of 200 μg/mL phosphonoacetic acid (lane 2) and in the presence of 400 μg/mL phosphonoacetic acid (lane 3). The blot was probed with luciferase mRNA, pp28 mRNA and beta-actin mRNA as indicated by the arrows. Panel C is an autoradiogram showing the results of a Western analysis using protein lysates prepared from pp28-luc cells 48 hours after infection with HCMV in the absence of viral DNA replication inhibitor (lane 4), in the presence of 200 μg/mL phosphonoacetic acid (lane 5) and in the presence of 400 μg/mL phosphonoacetic acid (lane 6). The blot was probed with antibodies specific against luciferase and pp28 proteins, as indicated by the arrows.
Figure 9B:
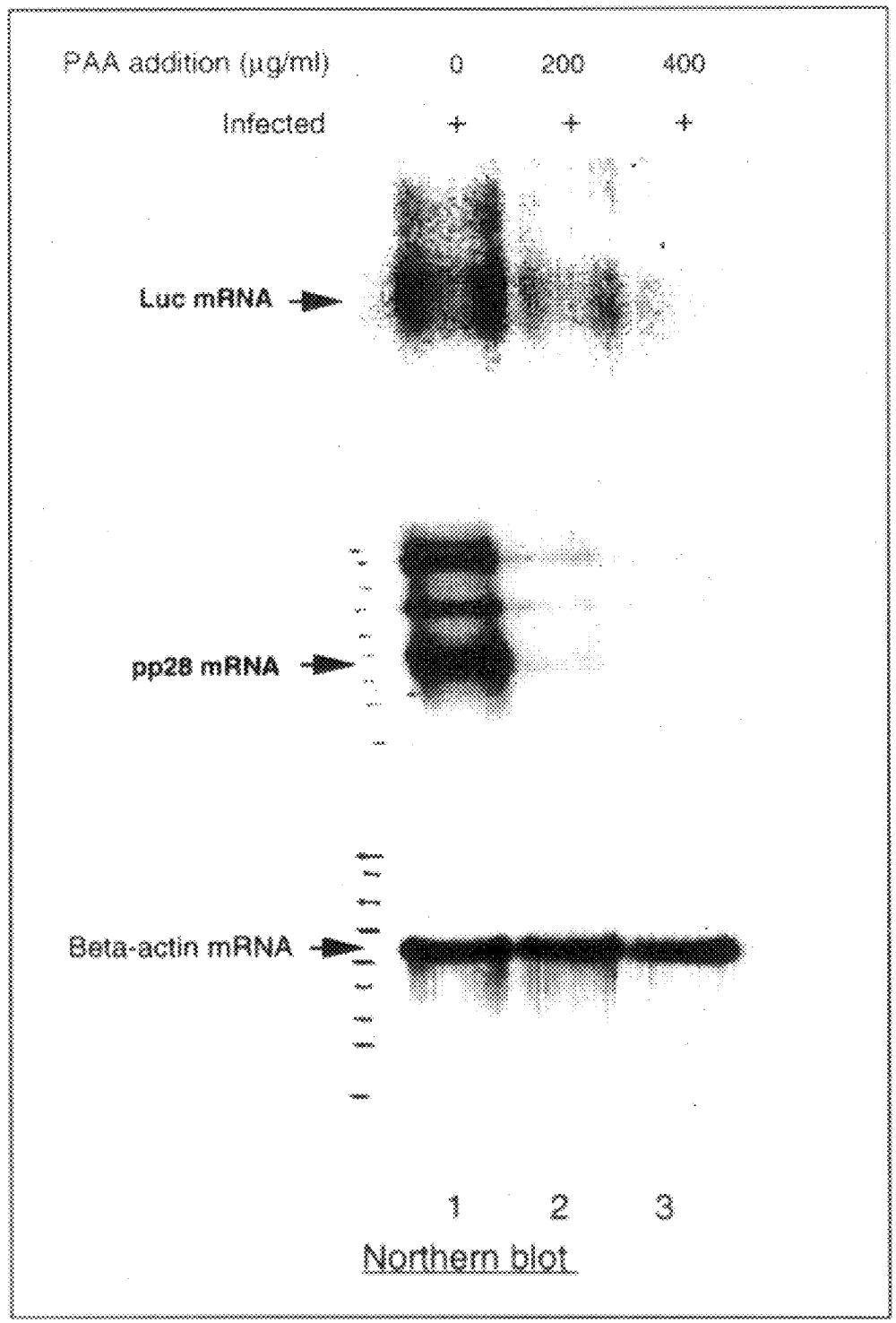
Figure 9C:
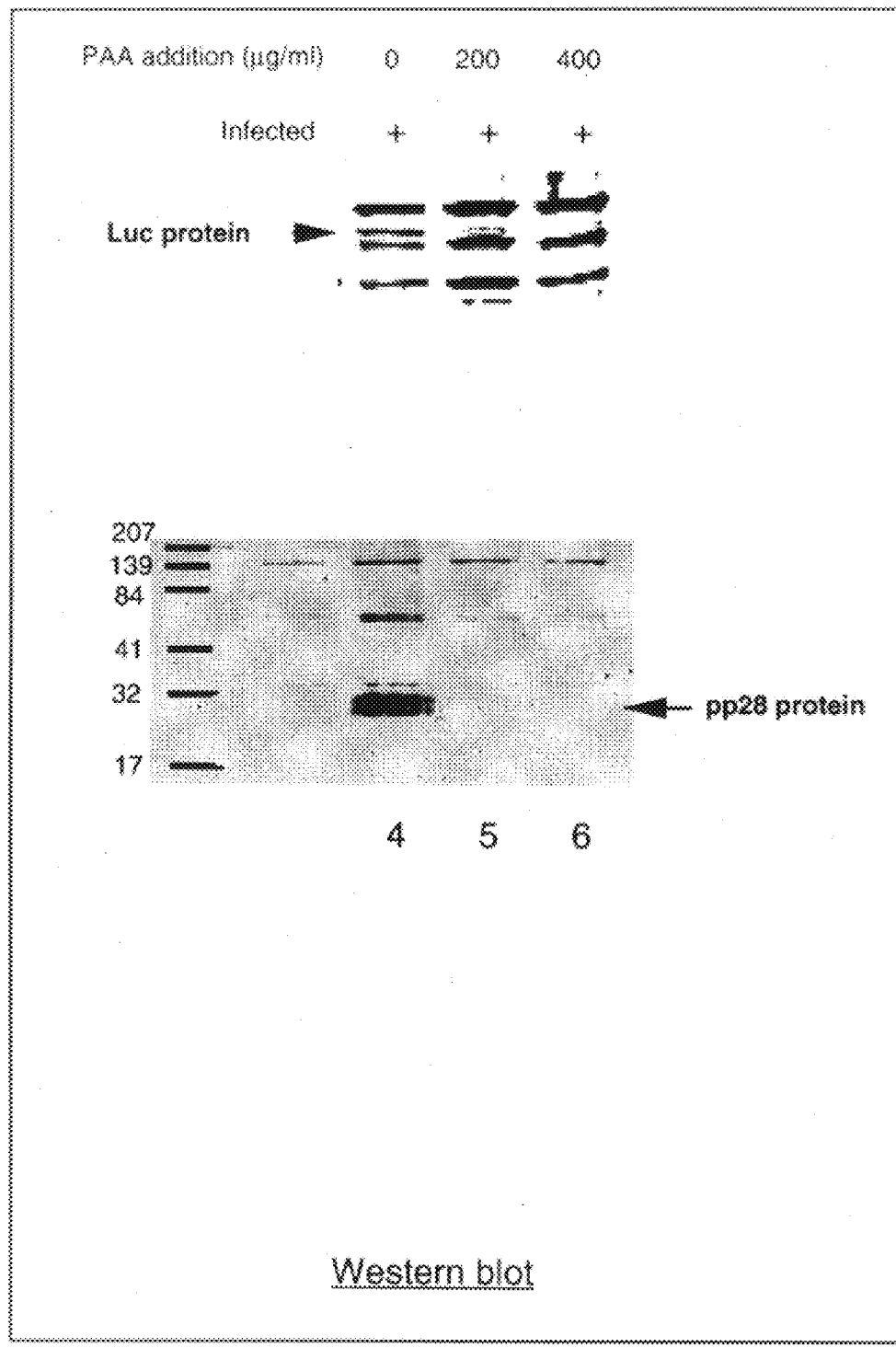

The response of the integrated reporter plasmids to HCMV infection was also examined in the presence and absence of the well characterized viral DNA inhibitor phosphonoacetic acid (PAA, Sigma, St. Louis, Mo., 99.7 purity). The results are presented in FIG. 7 (MIEP-luc), FIG. 8 (pol-luc) and FIG. 9 (pp28-luc). Cells were seeded into a 96 well plate in G418 selection media. The following day, cells were treated in the absence (lanes 1 and 4, panels B and C) or presence of PAA at 200 μg/mL (lanes 2 and 5, panels B and C) and 400 μ/mL (lanes 3 and 6, panels B and C). Cells were then superinfected with HCMV at 10 pfu/cell. Forty-eight hours post-infection, cells were harvested and isolated for either mRNA preparation, protein lysates or the luciferase assay. Luciferase activity measured as described above is shown in panels A of FIGS. 7–9. Northern analyses were performed on mRNA using probes for luciferase, MIEP-, pol- or pp28-specific mRNA and beta-actin MRNA to quantitate the amount of MRNA in each lane (panels B). Protein lysates were used for western blot analysis using antibody specific against luciferase (panels C). The inhibitory concentration of PAA (200–400 μg/ml) was not toxic to the U373 MG cells based on MTS cytotoxicity assay (data not shown). Viral DNA replication in presence of PAA was inhibited by nearly 90 percent as determined by dot blot analysis in three different stable clones (data not shown). The results indicate that inhibition of viral DNA replication has the same effect on luciferase expression as it does on endogenous viral gene expression. Accordingly, the cell lines can be used to identify inhibitors of the cascade of gene expression that occurs during natural viral infection.

Example 3

Specificity of Induction of Reporter Gene Expression

This Example illustrates the ability of the cell lines described in Example 1 to differentiate among different herpes viruses.

Figure 10A:
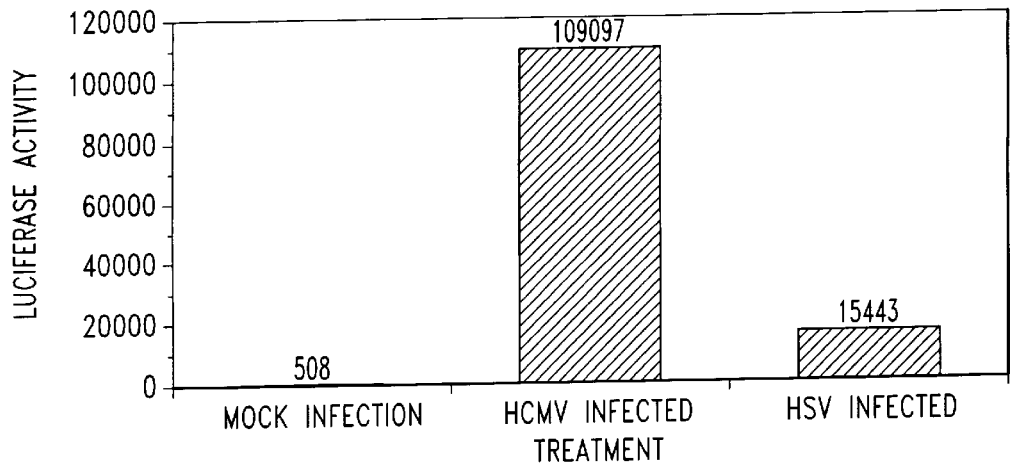
FIG. 10, panel A, is a graph depicting the luciferase activity detected in MIEP-luc cells without HCMV infection (column 1), after HCMV infection (column 2) and after HSV-1 infection (column 3). Panel B is a graph depicting the luciferase activity detected in pol-luc cells without HCMV infection (column 1), after HCMV infection (column 2) and after HSV-1 infection (column 3). Panel C is a graph depicting the luciferase activity detected in pp28-luc cells without HCMV infection (column 1), after HCMV infection (column 2) and after HSV-1 infection (column 3).
Figure 10B:
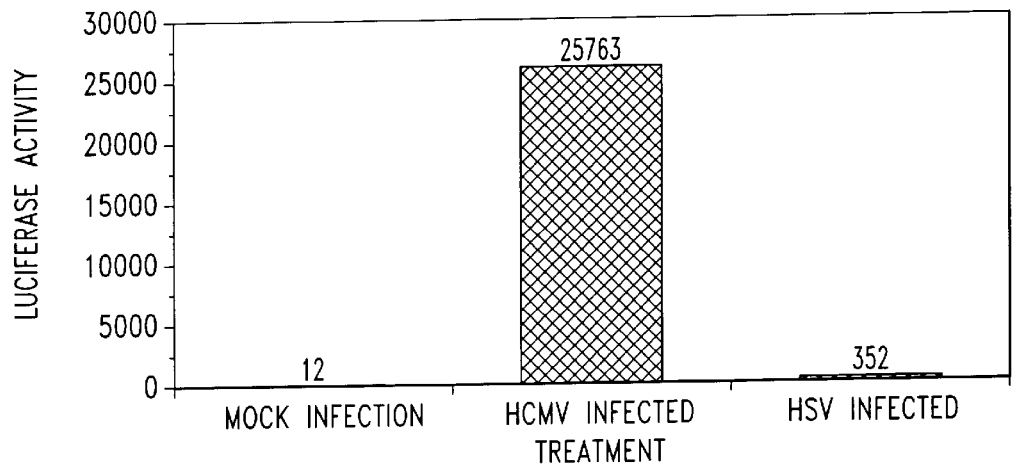
Figure 10C:
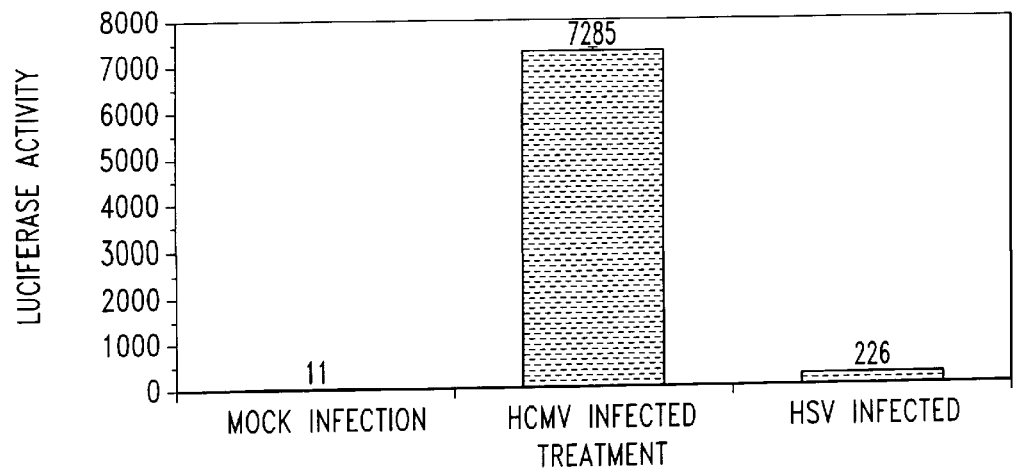
Figure 11:
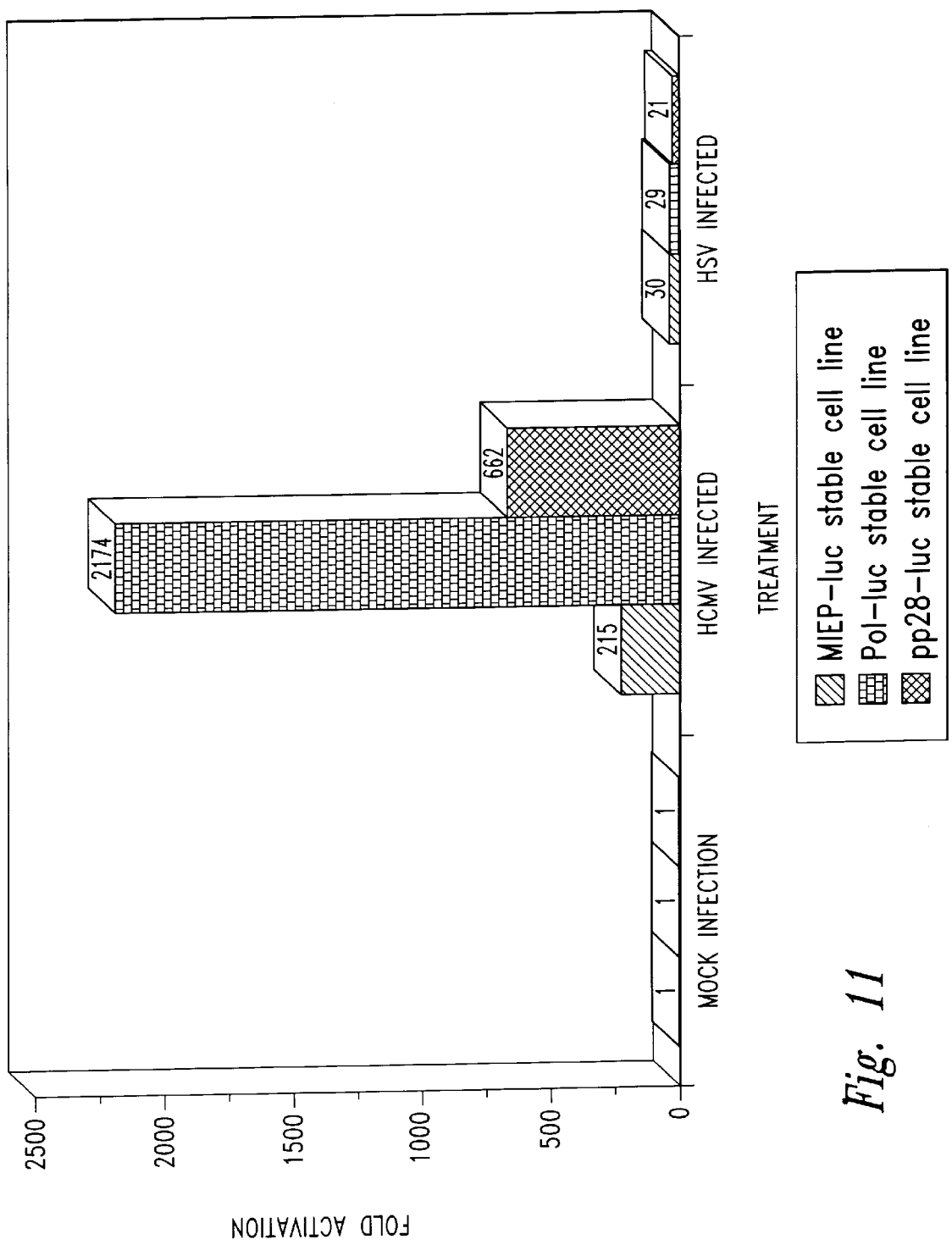
FIG. 11 is a graph showing the fold activation of luciferase activity for the MEP-luc (columns 1, 4 and 7), pol-luc (columns 2, 5 and 8) and pp28-luc (columns 3, 6 and 9) without infection (columns 1–3), upon HCMV infection (columns 4–6) and upon HSV-1 infection (columns 7–9).

The pattern of gene expression by different herpesviruses is similar, and the immediate early viral proteins appear to have related functions. Therefore, we were interested in finding out if the reporter system described above was specific for HCMV. We chose to compare the homologous cytomegalovirus with herpes simplex virus type 1 (HSV-1). The MIEP-luc, pol-luc and pp28-luc reporter cell lines were infected with HCMV (Towne strain) or HSV-1 (both purchased from ATCC) 3 pfu/cell and luciferase activity was quantified 48 hours postinfection. As shown in FIGS. 10 and 11, HCMV infection resulted in significant expression of luciferase while HSV infection only had a slight effect on expression of the reporter gene in each of these cell lines. Western blot analysis revealed that the HSV-1 gC protein, a late viral gene product, was efficiently expressed in HSV-1 infected U373 MG cells (data not shown). Therefore, while HSV-1 infects U373 MG cells and leads to expression of late phase genes, it does not efficiently induce the HCMV MIEP, pol or pp28 promoters, suggesting that activation of these promoters is virus specific. These results indicate that these cell lines may be used to specifically diagnose HCMV infection in a given sample.

Example 4

High Throughput Screen for Modulators of Viral Gene Expression

This Example illustrates the use of the cell lines of Example 1 for identifying inducers and inhibitors of viral gene expression.

Cells are maintained in DMEM (Mediatech, Herndon, Va.) supplemented with 10% fetal bovine serum (Gemini Bioproducts, Inc., Calabasas, Calif.), 1% antimycotic/ antibiotic (GIBCO, Baltimore, Md.) and 0.6 µg/mL G148 (GIBCO, Baltimore, Md.). Cells are seeded at $3\times10^4$ cells per well in flat-bottom, tissue culture treated 96-well plates (Corning, Corning, N.Y.) and incubated for about 18 hours in a 37° C. humidified environment. Appropriately diluted candidate modulators are then added directly to the media on cells to a final concentration of 10 µg/mL, and the plates incubated for 30 minutes at 37° C. HCMV (Towne strain, ATCC) is then added at 3 pfu/cell. Forty-eight hours post-infection, the cells are washed once with PBS (without $Ca^{++}$ and $Mg^{++}$) and lysed in the 96-well plate. An aliquot of the cell lysate is then transferred to a black 96-well plate (Packard, Hartford, Conn.) and luciferase assay reagent (Promega, Madison, Wis.) is added to the plate. Luciferase activity (luminescence) in each well is then measured using a Packard TopCount™.

Candidate modulators that result in luciferase activity that is approximately one-fold above the average mean signal obtained from cells incubated in the presence of virus, but in the absence of modulator are selected for further study as inducers of CMV gene expression. Candidate modulators generating a signal that is approximately 25%, preferably greater than 50% below the mean in the absence of modulator are inhibitors of CMV gene expression and have therapeutic potential as antiviral agents.

From the foregoing, it will be appreciated that, although specific embodiments of the invention have been described herein for the purpose of illustration, various modifications may be made without deviating from the spirit and scope of the invention.

We claim:

1. A method for detecting cytomegalovirus in a sample, comprising:
   (a) contacting a sample with a cell, wherein the cell is capable of being infected with cytomegalovirus and wherein the cell is stably transformed with a reporter gene operably linked to a cytomegalovirus promoter selected from the group consisting of the major immediate early promoter, the pol promoter and the pp28 promoter, wherein the promoter permits the detection of cytomegalovirus without detecting HSV-1; and
   (b) determining a level of expression of the reporter gene, relative to a predetermined level in the absence of sample, and thereby detecting cytomegalovirus in the sample.

2. The method of claim 1, wherein the reporter gene encodes an enzyme capable of being detected by a calorimetric, fluorimetric and/or luminometric assay.

3. The method of claim 1, wherein the reporter gene encodes a reporter protein selected from the group consisting of chloramphenicol acetyl transferase, beta-galactosidase, alkaline phosphatase and human growth factor.

4. The method of claim 1, wherein the reporter gene encodes luciferase.

5. The method of claim 1, wherein the cell is selected from the group consisting of human glial cells, immortalized human fibroblasts, human embryonic lung fibroblasts) human monocyte/macrophage cells and human endothelial cells.

6. The method of claim 1, wherein the sample is a biological sample isolated from a patient.

7. A method for monitoring the effectiveness of a therapy for CMV infection, comprising:
   (a) exposing a patient infected with CMV to a candidate therapy;
   (b) contacting a sample obtained from the patient with a cell, wherein the cell is capable of being infected with cytomegalovirus and wherein the cell is stably transformed with a reporter gene operably linked to a cytomegalovirus promoter selected from the group consisting of MIEP, pol and pp28; and (c) determining a level of expression of the reporter gene, relative to a predetermined level for cells contacted with a second sample obtained from the patient, wherein the second sample was obtained prior to the candidate therapy, and therefrom monitoring the effectiveness of the candidate therapy.

8. A method for evaluating the effect of a drug on CMV expression, comprising:

(a) exposing a sample obtained from a patient infected with CMV to a drug;

(b) contacting the sample with a cell, wherein the cell is capable of being infected with cytomegalovirus and wherein the cell is stably transformed with a reporter gene operably linked to a cytomegalovirus promoter selected from the group consisting of MIEP, pol and pp28; and (c) determining a level of expression of the reporter gene, relative to a predetermined level for cells contacted with a second sample obtained from the patient, wherein the second sample is not exposed to the drug, and therefrom evaluating the effect of the drug on CMV expression.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:1:

CGGGGTACCG CTGCAGTGAA TAATAAAATG                                  30

(2) INFORMATION FOR SEQ ID NO:2:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:2:

-continued

```
CGGGGTACCG TCACTCTTGG CACGGGGAAT C                                    31

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:3:

CCCAAGCTTG GGGAATTCAA CTCGTACAAG CAG                                  33

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:4:

CCCAAGCTTG GGTCAGACGA CGGTGGTCCC                                      30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

AAAGGTACCG CCGGCGTCTC GCCGGGCATC                                      30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

AAAAAGCTTG CCGGCCCAGC AGCTCGGGCG                                      30
```